United States Patent
Ahn et al.

(10) Patent No.: US 10,339,270 B2
(45) Date of Patent: Jul. 2, 2019

(54) BILLING SYSTEM FOR MEDICAL PROCEDURES

(75) Inventors: Sam S. Ahn, Los Angeles, CA (US); Hwa T. Kho, Agoura Hills, CA (US)

(73) Assignee: VASCULAR MANAGEMENT ASSOCIATES, INC., Los Angeles, CA (US)

( * ) Notice: Subject to any disclaimer, the term of this patent is extended or adjusted under 35 U.S.C. 154(b) by 360 days.

(21) Appl. No.: 13/103,129

(22) Filed: May 9, 2011

(65) Prior Publication Data

US 2011/0276348 A1    Nov. 10, 2011

Related U.S. Application Data

(60) Provisional application No. 61/332,902, filed on May 10, 2010.

(51) Int. Cl.
| | |
|---|---|
| *G06Q 50/00* | (2012.01) |
| *G06Q 30/00* | (2012.01) |
| *G06F 19/00* | (2018.01) |
| *G06Q 10/10* | (2012.01) |
| *G06Q 50/24* | (2012.01) |

(52) U.S. Cl.
CPC .......... *G06F 19/328* (2013.01); *G06Q 10/10* (2013.01); *G06Q 50/24* (2013.01)

(58) Field of Classification Search
USPC ............... 705/2–4, 34; 715/700–866
See application file for complete search history.

(56) References Cited

U.S. PATENT DOCUMENTS

| | | |
|---|---|---|
| 4,491,725 A | 1/1985 | Pritchard |
| 5,287,270 A | 2/1994 | Hardy et al. |
| 5,325,293 A | 6/1994 | Dorne |
| 5,809,476 A | 9/1998 | Ryan |
| 6,915,254 B1 | 7/2005 | Heinze et al. |
| 7,233,938 B2 | 6/2007 | Carus et al. |
| 2001/0041992 A1* | 11/2001 | Lewis et al. ............. 705/3 |
| 2003/0083903 A1* | 5/2003 | Myers ............. 705/2 |
| 2003/0146942 A1 | 8/2003 | Helgason et al. |
| 2003/0200119 A1* | 10/2003 | Lewis et al. ............. 705/2 |
| 2003/0220819 A1 | 11/2003 | Burstein et al. |

(Continued)

OTHER PUBLICATIONS

J. Goldsmith "Digital Medicine, Implications for Healthcare Leaders" (Health Administration Press, 2003, 199 pages).*

(Continued)

*Primary Examiner* — Mark Holcomb
(74) *Attorney, Agent, or Firm* — Snyder, Clark, Lesch and Chung, LLP

(57) ABSTRACT

A method may include outputting a graphical user interface (GUI), the GUI including a visual representation of at least a portion of the human body. The method may also include receiving input from a user via the GUI, the input selecting portions of the visual representation and medical procedures that were performed with respect to the selected portions, highlighting the selected portions of the visual representation and providing at least one of icons or text corresponding to the medical procedures that were performed. The method may further include automatically generating billing codes associated with the medical procedures that were performed and displaying the billing codes on the GUI.

18 Claims, 18 Drawing Sheets

(56) References Cited

U.S. PATENT DOCUMENTS

| | | | |
|---|---|---|---|
| 2004/0075433 A1 | 4/2004 | Kaufman | |
| 2004/0215634 A1 | 10/2004 | Wakefield et al. | |
| 2004/0254816 A1* | 12/2004 | Myers | 705/2 |
| 2007/0088564 A1 | 4/2007 | March, Jr. et al. | |
| 2008/0004505 A1* | 1/2008 | Kapit et al. | 600/300 |
| 2008/0033759 A1* | 2/2008 | Finlay | 705/3 |
| 2008/0065421 A1 | 3/2008 | Dang | |
| 2008/0133274 A1 | 6/2008 | Warner | |
| 2008/0273774 A1 | 11/2008 | Mikhail et al. | |
| 2010/0042435 A1 | 2/2010 | Kay | |
| 2010/0063848 A1 | 3/2010 | Kremer et al. | |

OTHER PUBLICATIONS

International Search Report and Written Opinion dated Oct. 27, 2011 issued in corresponding PCT application No. PCT/US2011/035700, 10 pages.

"ircoder.com," website information, print date Oct. 18, 2011, three pages.

\* cited by examiner

| Case Information | Vessel/Procedure View | Report Editor/Viewer |

| Patient First Name | John |
| Patient Last Name | Adam |
| Patient Date of Birth | 07/04/1774 |
| Patient ID | 000001 |
| Name of Surgeon | Benjamin Franklin |
| Assistant Surgeon | |
| Date of Service | 03/11/2011 |
| Start Time | AM 10 09 |
| End Time | AM 10 09 |
| Procedure ID | 7889 |
| Case Description | Balloon and stent of right subclavian |
| Site of Service | ⊙Office ○ASC ○Hospital |
| Anesthesia | ⊙Local Standby with Sedation ○Regional ○General |
| Access Type | ⊙Puncture ○Cut Down |
| Recent Angiogram | ⊙No Recent Angio ○Recent Angio/Clinical Change ○Recent Angio/Inadequate ○Recent Angio/No Change |
| Diagnostic code search | ⎯521 |
| Diagnostic Code List | 440.20 Atherosclerosis of extremity, unspecific ⎯522 |

| Save Case Info | Undo Unsaved Changes |

Common Codes

Arterial
- 433.10 - Carotid artery occlusion/stenosis w/o mention CL
- 433.11 - Carotid artery occlusion/stenosis w mention CL
- 440.0 - Atherosclerosis of aorta
- 440.1 - Atherosclerosis of renal artery
- 440.20 - Atherosclerosis of extremity, unspecific.
- 440.21 - Atherosclerosis w intermittent claudication
- 440.22 - Atherosclerosis w rest pain
- 440.23 - Atherosclerosis w ulceration
- 440.24 - Atherosclerosis w gangrene
- 440.29 - Atherosclerosis, other.
- 440.30 - Atherosclerosis of unspecified graft
- 440.31 - Atherosclerosis on auto vein bypass
- 440.32 - Athero of other nonaut vein bypass graft
- 440.4 - Chronic total occlusion of arteries of extremities
- 440.8 - Atherosclerosis of other spec vein
- 459.9 - Ischemia, leg
- 557.9 - Mesenteric Ischemia
- 443.9 - Unspecified peripheral vascular disease
- 443.0 - Raynaud's syndrome

Aneurysm
- 441.1 - Thoracic aneurysm, ruptured
- 441.2 - Thoracic aneurysm
- 441.3 - AAA, ruptured
- 441.4 - AAA
- 441.6 - Thoracoabdominal, ruptured
- 441.7 - Thoracoabdominal aneurysm
- 441.9 - Aortic aneurysms of unspecified site
- 442.0 - Aneurysm of renal artery
- 442.1 - Aneurysm of iliac artery
- 442.3 - Aneurysm of lower extremity
- 442.81 - Aneurysm of artery of neck
- 442.82 - Aneurysm of subclavian
- 442.83 - Aneurysm of splenic artery
- 442.84 - Aneurysm of other visceral artery
- 442.89 - Aneurysm, other

Comorbidity
- 585.6 - End stage renal disease
- 585.9 - Chronic renal insufficiency
- 427.31 - Atrial fibrillation
- 427.32 - Atrial flutter
- 427.9 - Unspecified cardiac dysrhythmia
- 496 - Chronic airway obstruction
- 428.0 - Congestive heart failure, unspecified
- 250.02 - Diabetes mellitus IDDM
- 250.00 - Diabetes mellitus NIDDM
- 401.9 - Hypertension
- 278.01 - Morbid obesity
- 344.1 - Paraplegia
- 344.0 - Quadriplegia, unspecified

Venous/Edema
- 453.8 - Deep vein thrombosis
- 454.0 - Varicose veins w ulcer
- 454.1 - Varicose veins w inflammation
- 454.2 - Varicose veins w ulcer and inflammation
- 454.8 - Varicose veins w other complications (edema)
- 454.9 - Varicose veins asymptomatic
- 457.1 - Lymphedema
- 459.81 - Venous insufficiency, unspecified
- 782.3 - Edema

Embolism/Thrombosis
- 444.0 - Abdominal aorta embolism/thrombosis
- 444.1 - Thoracic aorta embolism/thrombosis
- 444.21 - Upper extremity embolism/thrombosis
- 444.22 - Lower extremity embolism/thrombosis
- 444.81 - Iliac artery embolism/thrombosis
- 444.89 - Embolism/thrombosis, other
- 444.9 - Unspecified artery embolism/thrombosis
- 445.01 - Atheroembolism of upper extremity
- 445.02 - Atheroembolism of lower extremity
- 445.81 - Atheroembolism of kidney
- 445.89 - Atheroembolism of other site

Other
- 447.6 - Arteritis, unspecified
- 447.0 - Arteriovenous fistual, acquired
- 785.4 - Gangrene
- 446.5 - Giant cell arteritis
- 996.62 - Infection & inflammation reaction due to other
- 705.21 - Hyperhidrosis
- 729.5 - Limb pain
- 996.1 - Mechanical comp of vascular imp, dev
- 447.5 - Necrosis of artery
- 355.8 - Neuropathic pain, lower extremity
- 730.2 - Osteomyelitis
- 359.9 - Peripheral myopathy
- 337.2 - Reflex sympathetic dystrophy
- 435.2 - Subclavian steal syndrome
- 446.7 - Takayasu's disease
- 353.0 - Thoracic Outlet Syndrome
- 435.3 - Vertebrobasilar insufficiency Add Codes 526

FIG. 5C

| Case Information | Vessel/Procedure View | Report Editor/Viewer |
| Operative Report | Reimbursement Information |

Print Op Report

Patient Name: Adam, John
Patient ID#: 000001
Patient Date of Birth: 07/04/1774
Date of Operation: 03/11/2011
Procedure Start Time: 10:09 AM
Procedure End Time: 10:09 AM Pre-Op Diagnosis:
440.20 Atherosclerosis of extremity, unspecific.

Post-Op Diagnosis:

Operation Titles:
1. Puncture of right common femoral artery with ultrasound guidance
2. Catheterization of suprarenal aorta with aortogram
3. Selective catheterization of right subclavian artery with angiogram Surgeon: Benjamin Franklin
Assistant Surgeon:
Anesthesia: Local Standby with Sedation
Access Type: Puncture

Description of Procedure:
We visualized the right common femoral artery with ultrasound and found that the artery was patent. Then, under ultrasound visualization and guidance, we punctured the right common femoral artery. Images were taken and printed for documentation. We then used modified Seldinger's technique to insert a 6 French sheath. We catheterized the suprarenal aorta. We performed an aortogram on the suprarenal aorta (75625). Findings revealed 20% stenosis with calcification. We advanced the catheter into the right subclavian artery. We performed an angiogram on the right subclavian artery (75710). Findings revealed 80% stenosis with calcification, plaque. We balloon dilated the right subclavian artery (35475,75962). Pre-treatment stenosis was 80%, with calcification, plaque. Post-treatment stenosis was 50%, with calcification, plaque. We put a stent in the right subclavian artery (37205,75960). Pre-treatment stenosis was 50%, with calcification, plaque. Post-treatment stenosis was 0%, with calcification, plaque. We then closed the right common femoral artery with a Perclose closure device (G0269).

FIG. 6A

Additional Information:

Complication:
Estimated blood loss:
Contrast Type:

Contrast Amount:
Heparin Dose:
Condition of Patient:
Disposition of Patient:
Fluoro Time:
Notes:

Signature: Benjamin Franklin

X _____

| BILLABLE CODES | | |
|---|---|---|
| angiogram | suprarenal aorta | 75625 |
| catheter | right subclavian artery | 36216 |
| angiogram | right subclavian artery | 75710 |
| pta | right subclavian artery | 35475 |
| pta | right subclavian artery | 75962 |
| stent | right subclavian artery | 37205 |
| stent | right subclavian artery | 75960 |
| closure | suprarenal aorta | G0269 |

FIG. 6B

BILLING SYSTEM FOR MEDICAL PROCEDURES

RELATED APPLICATION

This application claims priority under 35 U.S.C. § 119 based on U.S. Provisional Patent Application No. 61/332,902 filed May 10, 2010, the disclosure of which is hereby incorporated herein by reference.

BACKGROUND INFORMATION

In the medical profession, generating bills for services performed on a patient is time consuming. For example, in a typical scenario, a surgeon may perform a procedure on a patient. After the procedure, the surgeon will dictate operation notes or generate handwritten notes regarding what procedures were performed and give these notes to his/her staff. The staff will then attempt to generate billing codes associated with each procedure that was performed. These billing codes may correspond to approved billing codes used by an insurance provider.

Generating bills in this manner is not only costly with respect to the time spent generating a bill, but prone to errors due to multiple parties being involved in generating the bill. For example, the doctor's notes may be poorly organized or presented, may include non-standard medical terminology, and/or may be partially provided in a language other than the primary language of the staff person generating the bill. Still another problem associated with generating bills in this manner is that the doctor may be unable to recall all of the procedures that were performed on the patient.

BRIEF DESCRIPTION OF THE DRAWINGS

FIGS. 5A-5L are exemplary user interface screens associated with the billing program of FIG. 3; and FIGS. 6A and 6B are diagrams associated with an exemplary report generated by the billing program of FIG. 3.

DETAILED DESCRIPTION OF PREFERRED EMBODIMENTS

The following detailed description refers to the accompanying drawings. The same reference numbers in different drawings may identify the same or similar elements. Also, the following detailed description does not limit the invention. Instead, the scope of the invention is defined by the appended claims and their equivalents.

Implementations described herein allow medical personnel to document medical procedures and automatically generate billing information associated with the procedure. For example, in one implementation, a computer program may include a graphical user interface (GUI) that allows a doctor or other medical professional to easily enter information regarding medical procedures performed on a patient. The GUI may provide a visual representation of a human body and allow the doctor to use a mouse, stylus, keyboard, voice recognition software or other input device to enter information with respect to the visual representation of the body. The computer program may automatically store the user entered information to create a record of the procedures performed by the doctor. The computer program may also automatically generate billing codes to bill the procedures, as described in detail below.

Figure 1:
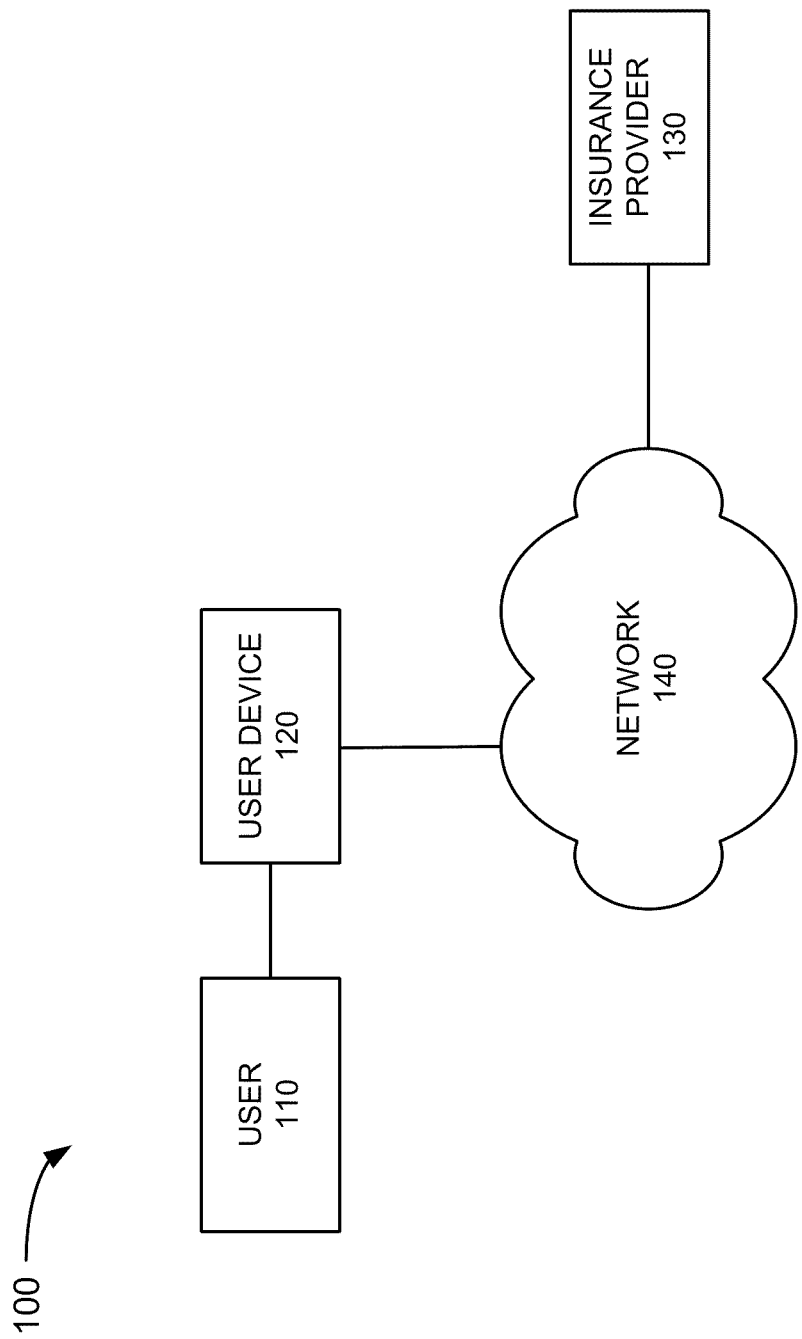
FIG. 1 illustrates an exemplary environment in which concepts described herein may be implemented.

FIG. 1 illustrates an exemplary environment 100 in which embodiments described herein may be implemented. Referring to FIG. 1, environment 100 may include user 110, user device 120, insurance provider 130 and network 140. In an exemplary implementation, user 110 may represent a doctor, nurse, medical professional or other party associated with inputting information to user device 120.

User device 120 may include a computing device, such as a personal computer (PC), laptop computer, server, remote terminal, mobile terminal, smart phone, notebook computer, netbook computer, tablet computer, personal digital assistant (PDA), etc. User 110 may interact with user device 120 during or after a medical procedure to input information associated with a procedure, as described in more detail below.

Insurance provider 130 may represent an insurance company or other entity to which bills are to be forwarded. Network 140 may include one or more wired, wireless and/or optical networks that are capable of receiving and transmitting data, voice and/or video signals, including multi-media signals that include voice, data and video information. For example, network 140 may include one or more public switched telephone networks (PSTNs), one or more wireless networks, one or more satellite networks, one or more packet switched networks, such as an IP-based network, a local area network (LAN), a wide area network (WAN), a personal area network (PAN) (e.g., a wireless PAN), an intranet, the Internet, or another type of network that is capable of transmitting data. In some implementations, user device 120 may forward bills to insurance provider 130 via network 140.

The exemplary configuration illustrated in FIG. 1 is provided for simplicity. It should be understood that a typical environment may include more or fewer devices than illustrated in FIG. 1. For example, in some implementations, environment 100 may include a medical records storage system where a doctor's notes and/or other information regarding medical procedures may be forwarded and stored, a health information system which stores and tracks patient information, a revenue management system that links to accounting or billing systems of one or more doctors/medical practices, a claims clearing house which acts as an intermediary to submit bills/invoices to various entities (e.g., insurance provider 130) that will pay for a doctor's services, and/or other systems that aid in generating, storing and processing medical and billing information. Also, in some instances, one or more of the components of environment 100 may perform one or more functions described as being performed by another one or more of the components of environment 100.

Figure 2:
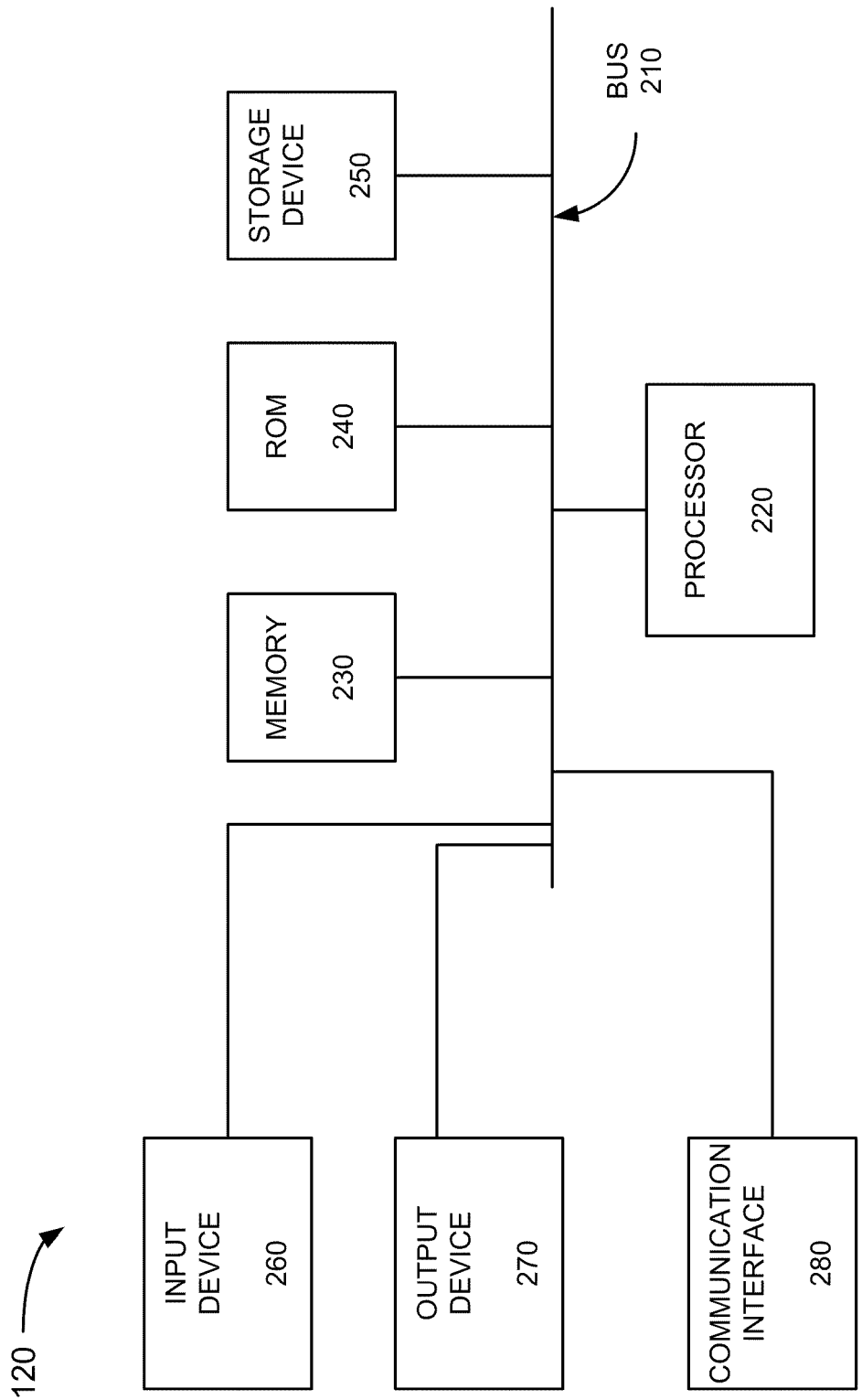
FIG. 2 illustrates an exemplary configuration of the user device of FIG. 1.

FIG. 2 illustrates an exemplary configuration of user device 120. Referring to FIG. 2, user device 120 may include bus 210, processor 220, main memory 230, read only memory (ROM) 240, storage device 250, input device 260, output device 270, and communication interface 280. Bus 210 may include a path that permits communication among the elements of user device 120.

Processor 220 may include a processor, microprocessor, application specific integrated circuit (ASIC), field programmable gate array (FPGA) or processing logic that may interpret and execute instructions. Memory 230 may include a random access memory (RAM) or another type of dynamic storage device that may store information and instructions for execution by processor 220. ROM 240 may include a ROM device or another type of static storage device that may store static information and instructions for use by processor 220. Storage device 250 may include a magnetic and/or optical recording medium and its corresponding drive.

Input device 260 may include a mechanism that permits an operator to input information to user device 120, such as a keyboard, a keypad, control keys, a mouse, a pen, voice recognition and/or biometric mechanisms, etc.

Output device 270 may include a mechanism that outputs information to the operator, including a display, a printer, a speaker, etc. For example, output device 270 may include a display screen (e.g., a liquid crystal display (LCD), a light emitting diode (LED) display or another type of display) that provides information to user 110, as discussed in more detail below.

Communication interface 280 may include a transceiver that enables user device 120 to communicate with other devices and/or systems. For example, communication interface 280 may include a modem or an Ethernet interface to a LAN or other mechanisms for communicating via a network, such as network 140. Communication interface 280 may also include a radio frequency (RF) interface that allows user device 120 to communicate wirelessly via network 140.

User device 120 may perform processing associated with displaying information to a user via a GUI, receiving input via the GUI and processing the information. According to an exemplary implementation, user device 120 may perform these operations in response to processor 220 executing sequences of instructions contained in a computer-readable medium, such as memory 230. A computer-readable medium may be defined as a physical or logical memory device.

The software instructions may be read into memory 230 from another computer-readable medium, such as storage device 250, or from another device via communication interface 280. The software instructions contained in memory 230 may cause processor 220 to perform processes that will be described later. Alternatively, hard-wired circuitry may be used in place of or in combination with software instructions to implement processes described herein. Thus, implementations described herein are not limited to any specific combination of hardware circuitry and software.

Figure 3:
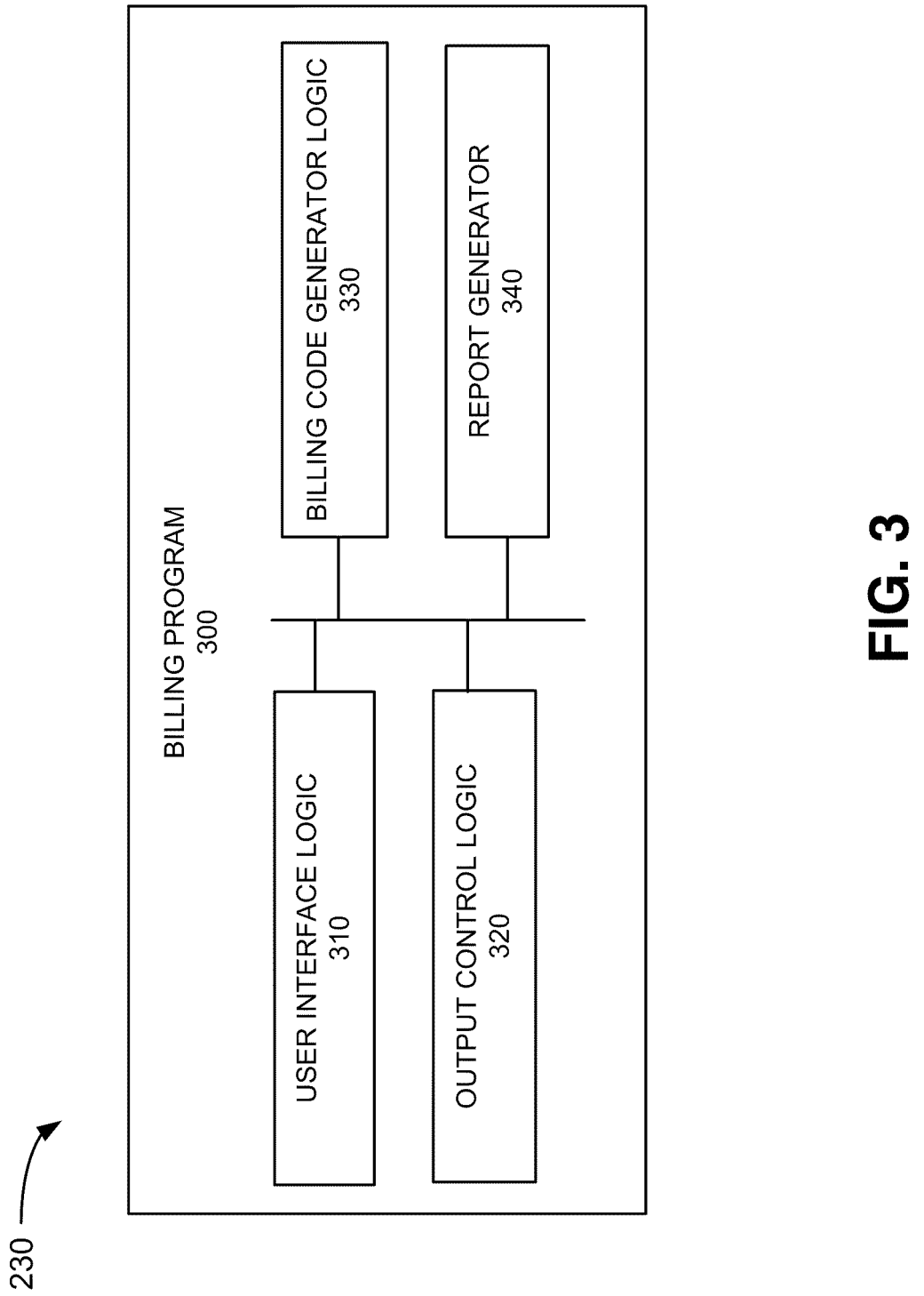
FIG. 3 illustrates exemplary logic components implemented in a billing program consistent with implementations described herein.

FIG. 3 is an exemplary functional block diagram of components implemented in user device 120 of FIG. 2. In an exemplary implementation, all or some of the components associated with billing program 300 illustrated in FIG. 3 may be stored in memory 230. For example, all or some of the components associated with billing program 300 may be implemented by processor 220 executing one or more programs stored in memory 230.

Billing program 300 may include a software program executed by processor 220 that provides a user (e.g., a doctor) with a visual or graphical interface for entering information regarding a procedure. Billing program 300 may automatically generate billing-related information, as well as allow the user to edit the information, as described in detail below. Referring to FIG. 3, in an exemplary implementation, billing program 300 may include user interface logic 310, output control logic 320, billing code generator logic 330 and report generator 340. Billing program 300 and its various logic components are shown in FIG. 3 as being included in user device 120. In alternative implementations, these components or a portion of these components may be located externally with respect to user device 120. For example, in some implementations, one or more of the components of billing program 300 may be located in or executed by other devices in network 100 (e.g., insurance provider 130 or in another device).

User interface logic 310 may provide a GUI to be output via output device 270, such as an LCD. In an exemplary implementation, the GUI may provide a visual representation of the human body, including major organs, vascular system, etc. User interface logic 310 may receive input from a user via input device 260, which may include a mouse, a stylus, a keyboard, a keypad, etc. In some implementations, user interface logic 310 may include speech recognition logic to perform speech recognition on voice data provided by the user and covert the voice data from the user into text data for input to billing program 300.

Output control logic 320 may receive information entered via the GUI and modify the visual representation based on the input. For example, a doctor may provide input on the visual representation of the human body provided by user interface logic 310, which will then illustrate the input graphically/visually, as described in more detail below. Output control logic 320 may also provide prompts to allow the doctor/user to enter additional information, such as text-based notes associated with each procedure, as described in more detail below.

Billing code generator logic 330 may store billing codes associated with various medical procedures. For example, in one implementation, billing code generator logic 330 may include a table of codes that correspond to Healthcare Common Procedure Coding System (HCPCS) codes. HCPCS codes are used by many insurance providers, and bills/invoices submitted to the insurance providers are typically required to itemize services performed using HCPCS codes. In other implementations, billing code generator logic 330 may store codes that are used by a particular insurance provider. In addition, in some implementations, billing code generator logic 330 may include a number of tables of different codes that may be used for different purposes, such as for different third party payers (e.g., insurance companies). Further, in some instances, billing code generator logic 330 may include tables of codes based on the location in which the services are performed and/or billed. For example, in some states or countries, different types of codes may be used to satisfy particular billing related requirements. In such cases, the tables of codes may correspond to the particular location in which the services are performed. In each case, billing program 300 may update the codes on a periodic basis to ensure that the codes are accurate.

Billing code generator logic 330 may receive information input by the user via the GUI, access the billing code table and generate billing information based on the inputted information. In an exemplary implementation, billing code generator logic 330 may automatically generate billing codes used by various insurance companies, such as HCPCS codes. This may aid in simplifying the generation of bills, as well as facilitate easier payment by the third party.

Report generator 340 may store text-based reports associated with procedures entered by the user. For example, report generator 340 may generate a report based on information entered via the GUI. This may provide the doctor with a complete record of each procedure that was performed, as described in detail below.

Figure 4:
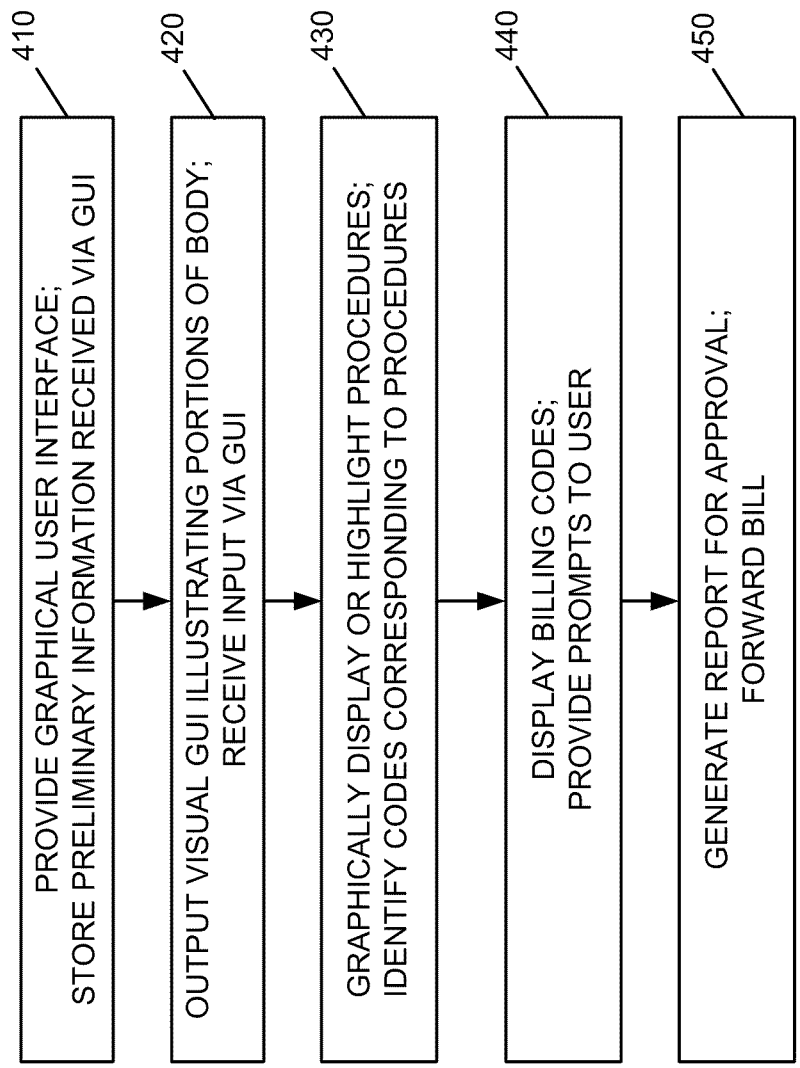
FIG. 4 is a flow diagram illustrating exemplary processing associated with interacting with the billing program of FIG. 3.
Figure 5A:
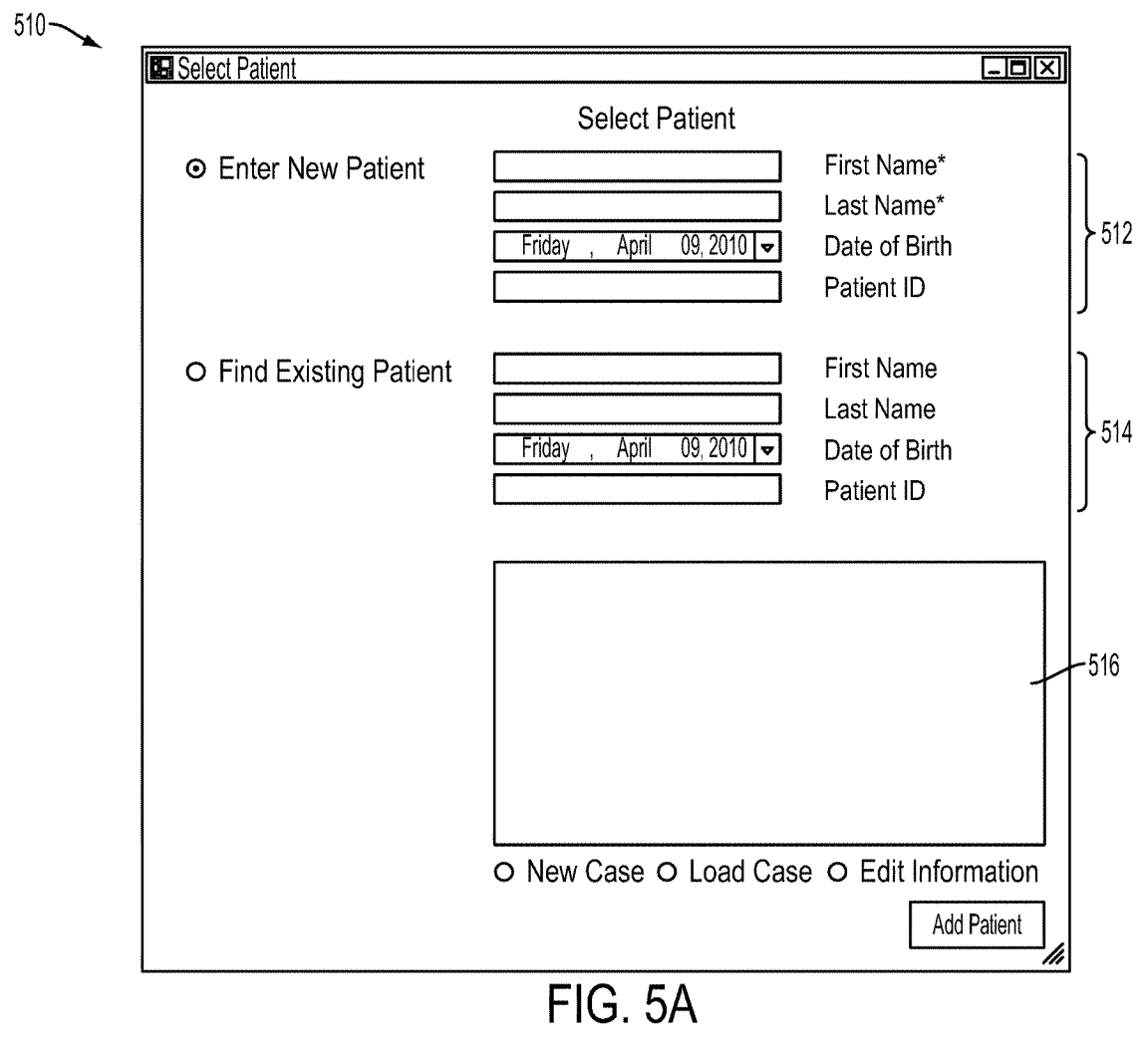

FIG. 4 is a flow diagram illustrating exemplary processing associated with interacting with billing program 300. In this example, assume that user 110 is a vascular surgeon who has just finished performing surgery on a patient. Processing may begin with user 110 (also referred to as surgeon or surgeon 110) accessing billing program 300 on user device 120. Billing program 300 may provide a GUI to allow the surgeon to enter preliminary information via the GUI (block 410). For example, user interface logic 310 may output a "select patient" GUI 510, as illustrated in FIG. 5A. GUI 510 may include input boxes at area 512 that allows the surgeon to enter the patient's name, birth date, patent identifier (ID), etc. GUI 510 may also include input boxes at area 514 that allows the surgeon to retrieve information regarding an existing patient. GUI 510 may further include text area 516 that allows the surgeon to enter additional information or notes regarding the patient. After entering the information via GUI 510, billing program 300 may store the information in, for example, report generator 340 (act 410).

After receiving and storing the preliminary information regarding the patient, user interface logic 310 may provide GUI 520, as illustrated in FIG. 5B. GUI 520 may include case information input boxes that allows the surgeon to enter various information, such as the name of the surgeon, assistant surgeon, date of procedure, start time, end time, procedure ID, case description, site of service, whether anesthesia was given, access type, whether a recent angiogram was performed, etc. GUI 520 may also include a diagnostic code search box 521 and a diagnostic code list area 522. User 110 may use search box 521 to search for a code corresponding to a particular diagnosis, such as atherosclerosis.

For example, user interface logic 310 may store a table of diagnostic codes, as illustrated by table 524 in FIG. 5C. Referring to FIG. 5C, table 524 may include a listing of common codes for a large number of patient related problems, such as problems related to arterial issues, aneurysms, comorbidity, venous/edema, embolism/thrombosis, etc. Table 524 may also allow the user to add codes, as illustrated by the "add codes" input button 526.

In this example, the user 110 may enter the term "atherosclerosis" and output control logic 320 may provide a listing of a number of diagnoses associated with the term atherosclerosis, such as codes 440.0, 440.1, 440.20, 440.21, 440.22, etc., illustrated in table 524. User 110 may select the appropriate diagnostic code and the selected code will be provided in diagnostic code list area 522.

For example, the surgeon may select code 440.20 from a number of codes displayed to the surgeon and the corresponding information may be provided in diagnostic code list area 522, as illustrated in FIG. 5B. This allows user 110 to be able to easily provide the diagnostic information without having to remember particular diagnostic codes. In other instances, user 110 may access table 524 and select the particular code of interest without using diagnostic code search box 521. In still other instances, user 110 may know the particular code he/she wishes to enter and manually enter the diagnostic code in area 522. Providing diagnostic information prior to any medical procedure may be useful in creating a medical history associated with the patient. After the surgeon has entered the desired information via GUI 520, billing program 300 may receive the information and store the information in report generator 340 (block 410).

Figure 5D:
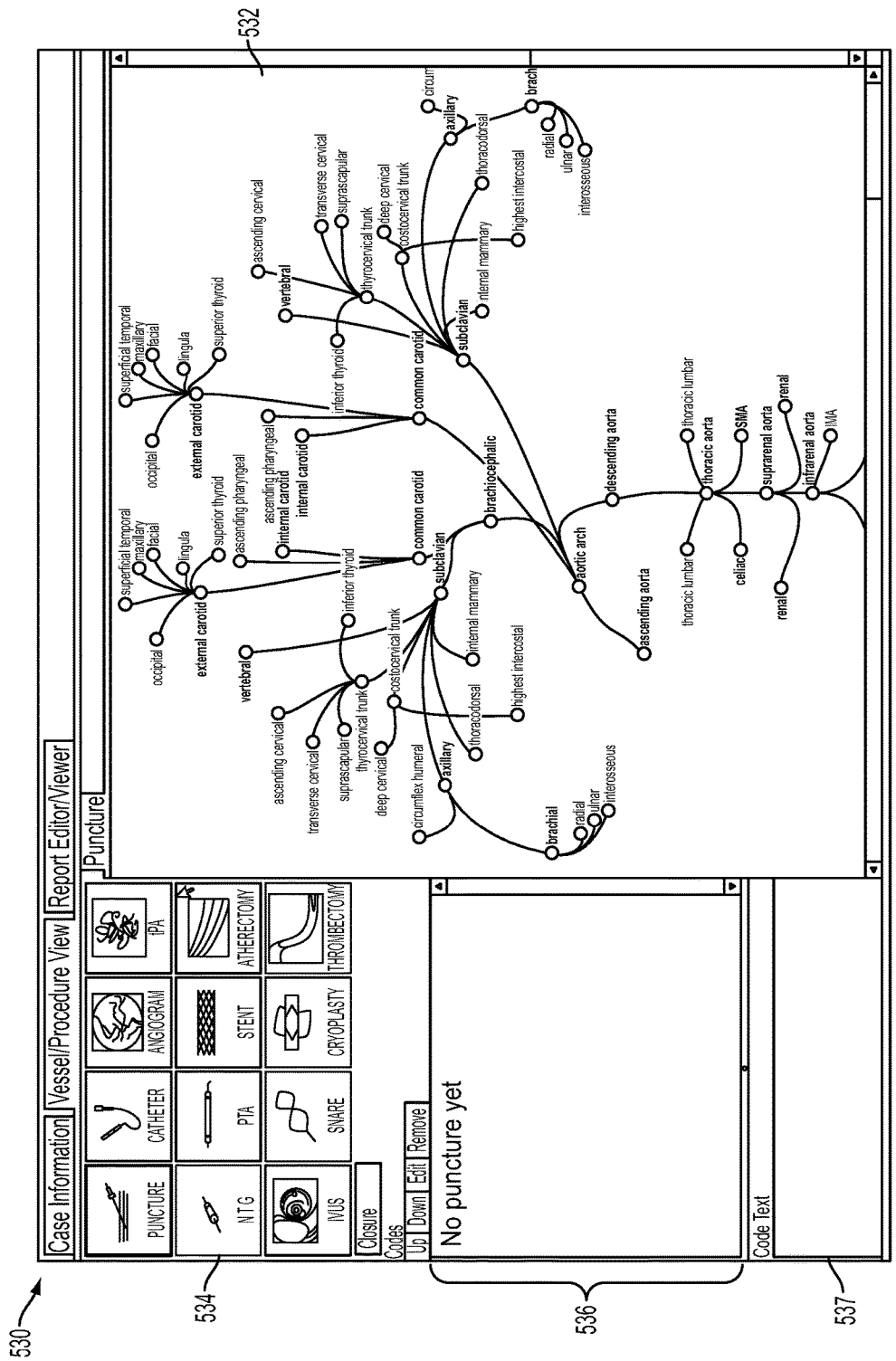

User interface logic 310 may then provide a GUI that includes a visual representation of a portion of the human body (block 420). For example, continuing with the example above in which the doctor is a vascular surgeon, user interface logic 310 may provide GUI 530 illustrated in FIG. 5D. Referring to FIG. 5D, GUI 530 includes a visual representation of the human vascular system at area 532. GUI 530 may also include a number of procedures illustrated at area 534, a codes area 536 and a text area 537. The visual representation of the vascular system at area 532 may display major and minor arteries, veins, organs, etc. Procedure area 534 may provide a visual representation or icons and/or text representation of common surgical procedures, such as puncture, catheter, angiogram, tPA, NTG, PTA, stent, atherectomy, IVUS, snare, cryoplasty, thrombectomy, closure, etc. Code area 536 may include an area in which medical codes (e.g., HCPCS codes) associated with a procedure are displayed in response to input provided at area 532. Code text area 537 may include an area to enter notes and text associated with a procedure, as described in detail below. In FIG. 5D, no codes are indicated in area 536 since the user has not input data regarding the procedure. In some implementations, area 536 may display a note, such as "no puncture yet," as indicated in FIG. 5D to indicate that the procedures performed by the surgeon have not been started.

Figure 5E:
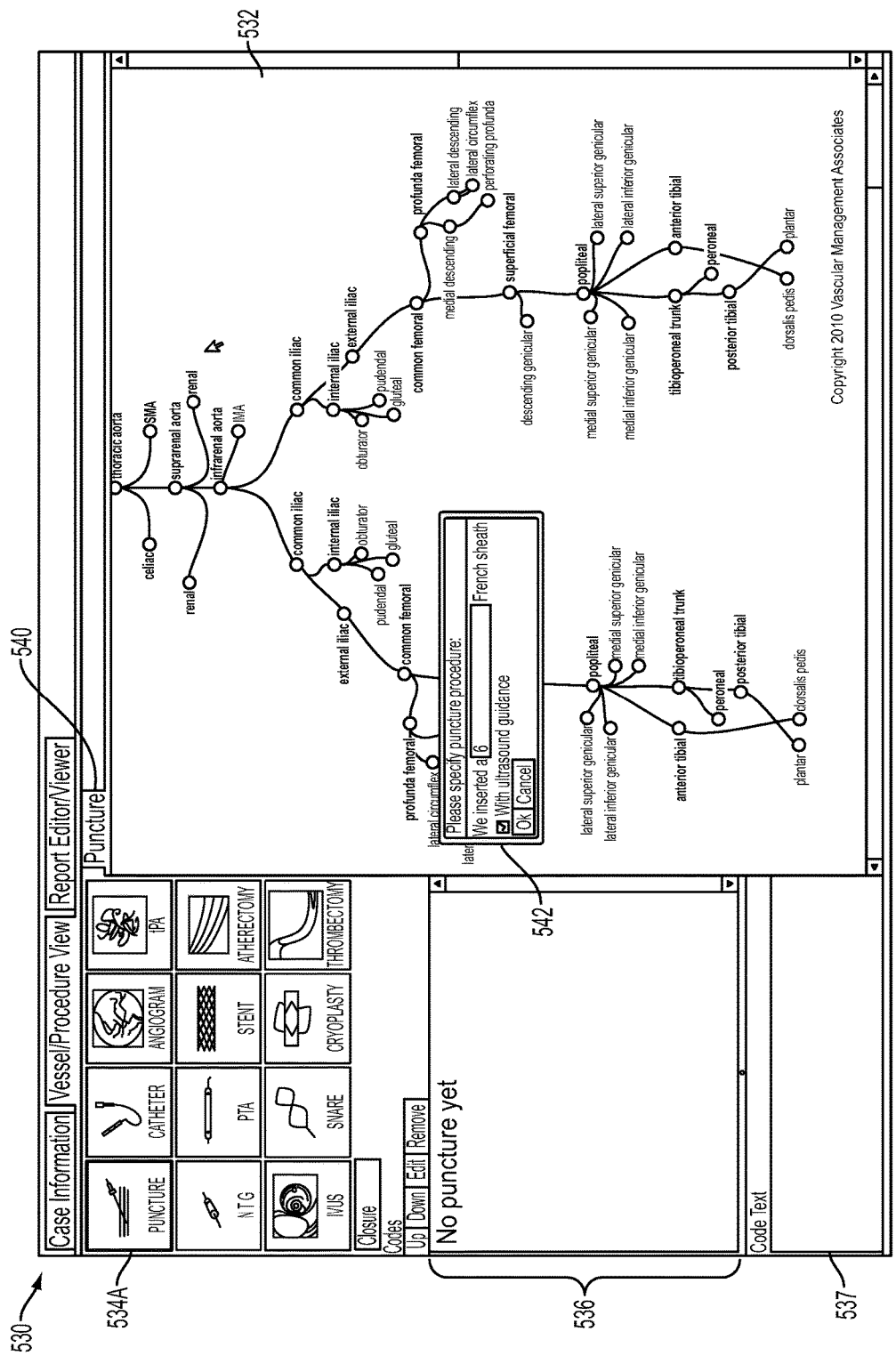

Assume that the surgeon begins interacting with GUI 530 to record information associated with a recently completed surgical procedure (block 420). In this case, the surgeon may use input device 260, such as a mouse, stylus, keyboard, cursor controller or other input mechanism, to select puncture icon 534A (in area 534) identifying a puncture procedure. User interface logic 310 may receive the selection and output puncture screen 540 in area 532, as illustrated in FIG. 5E. After the surgeon selects puncture icon 534A, puncture screen 540 may provide a pop-up or dialog window/box 542 which prompts the user (e.g., surgeon in this example) to specify a type of puncture procedure. For example, pop-up window 542 may prompt the surgeon to enter relevant information associated with the particular procedure. In this example, pop-up window 542 may prompt the surgeon to enter information regarding the type of sheath used, whether ultrasound guidance was used during the procedure, etc. Puncture screen 540 may also continue to display a visual representation of the arterial system of a patient, as illustrated in area 532.

Figure 5F:
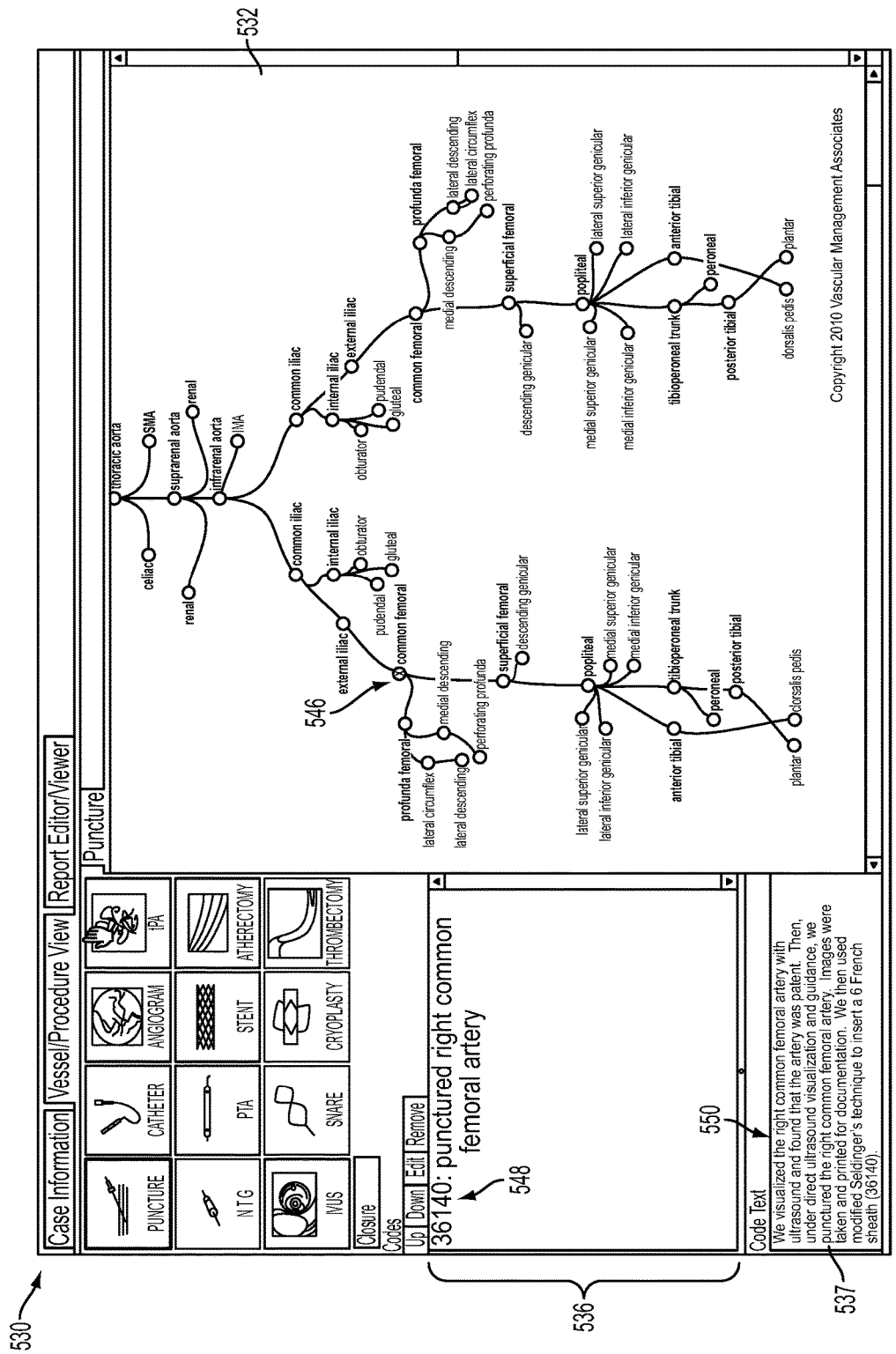

After the surgeon has entered the appropriate information via pop-up window 542, assume that the surgeon selects/clicks on the right common femoral artery (e.g., by clicking on the area/circle representing the right common femoral artery, illustrated as 546 located on visual representation 532 in FIG. 5F. This location may correspond to a location of a procedure performed at the start of the surgery. After selecting the right common femoral artery, output control logic 320 may highlight the right common femoral artery in a color, such as red or green, via bolding, by placing an X in the small circle representing the right common femoral artery, and/or via some other visual effect that provides prominence to the selected portion (block 430).

Billing code generator logic 330 may also automatically identify codes corresponding to the puncture procedure (block 430). For example, billing code generator logic 330 may perform a lookup to identify a code corresponding to puncturing the right common femoral artery that was inputted via GUI 530 (block 430). For example, as described previously, billing code generator logic 330 may include a table of codes that correspond to various procedures. As described previously, these codes may correspond to HCPCS codes or other codes associated with an insurance provider. In this example, assume that the codes stored in the table in billing code generator logic 330 are HCPCS codes.

Output control logic 320 may receive the billing code from billing code generator logic 330 and display the identified code corresponding to puncturing the right common femoral artery in area 536 (block 440). For example, output control logic 320 may display a code labeled 548 in FIG. 5F, along with text that identifies the particular procedure. In this example, output control logic 320 may output the following: 36140: punctured right common femoral artery, for display at area 536. Code 36140 may correspond to an HCPCS code for puncturing the right common femoral artery. The description following code 36140 may provide a brief description corresponding to the code (e.g., punctured right common femoral artery).

Output control logic 320 may also prompt the surgeon to enter additional text in area 537 (block 440). For example, the surgeon may enter text (labeled 550 in FIG. 5F) in area 537 regarding the procedure. Text 550 may act as a running narrative of the actions associated with puncturing the right common femoral artery. Text 550 may also include information that identifies a procedure or portion of a procedure that may be billed to a third party (e.g., insurance provider 130) or to enhance a bill provided to the third party. For example, if a particular procedure identified via GUI 530 required additional or special procedures due to a particular medical condition or difficulty associated with the patient, this information may be provided in text 550 at area 537.

In some implementations, some or all of the text 550 illustrated at area 537 may be automatically provided by output control logic 320 based on information provided, for example, via pop-up window 542. As an example, the surgeon entered information indicating via pop-up window 542 indicating that a 6 French sheath was used for the puncture and that the procedure was performed using ultrasound guidance. In this implementation, output control logic 320 may automatically pre-populate text area 537 with this information and the surgeon may augment this information, as necessary. The information in text area 537 may act as operation notes that provide a chronologically accurate narrative of the operation and/or other medical procedures performed on the patient.

For example, report generator 340 may use text displayed in area 537 to generate a narrative that will act as a surgeon's operation notes identifying the procedures that were performed on the patient in chronological order. This narrative, or a portion of this narrative, may be included in a report that will provide information needed to meet third party payer requirements, such as requirements associated with insurance provider 130, as described in more detail below. The report may also include information that conforms with standard clinical requirements regarding documenting medical procedures.

The surgeon may then select another one of input elements provided at procedure area 534 corresponding to the procedure performed on the right common femoral artery. As an example, the surgeon may select the catheter icon, labeled 534B in FIG. 5G. The surgeon may then click on/select the location of the end points associated with the catheterization using the visual representation provided at area 532. For example, assume that the surgeon selects the suprarenal aorta as the end point. In this case, output control logic 330 may highlight the path of the vessels that were catheterized, as illustrated in bold and labeled 552 in area 532 of FIG. 5G.

Figure 5G:
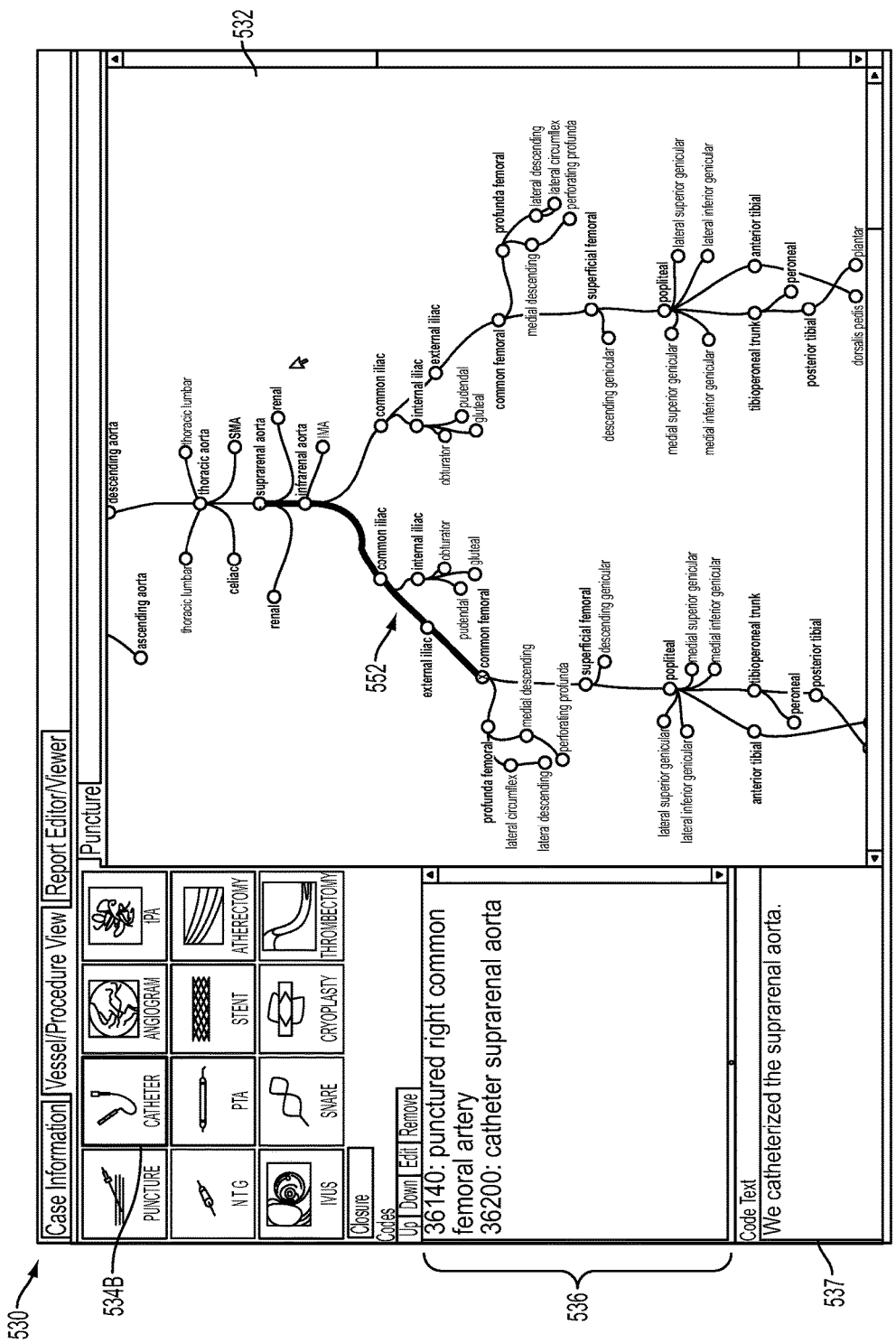

Billing code generator logic 330 may also automatically identify a code (e.g., an HCPCS code) associated with the catheterization of the suprarenal aorta and output control logic 320 may display the code at area 536, as illustrated in FIG. 5G. In this example, output control logic 320 may display code 36200, along with text indicating that the suprarenal aorta was catheterized, as also illustrated in FIG. 5G. Similar to the discussion above with respect to the puncture procedure, user interface logic 310 may also prompt the surgeon to enter text associated with this portion of the procedure that will be displayed at area 537, as also illustrated in FIG. 5G.

Figure 5H:
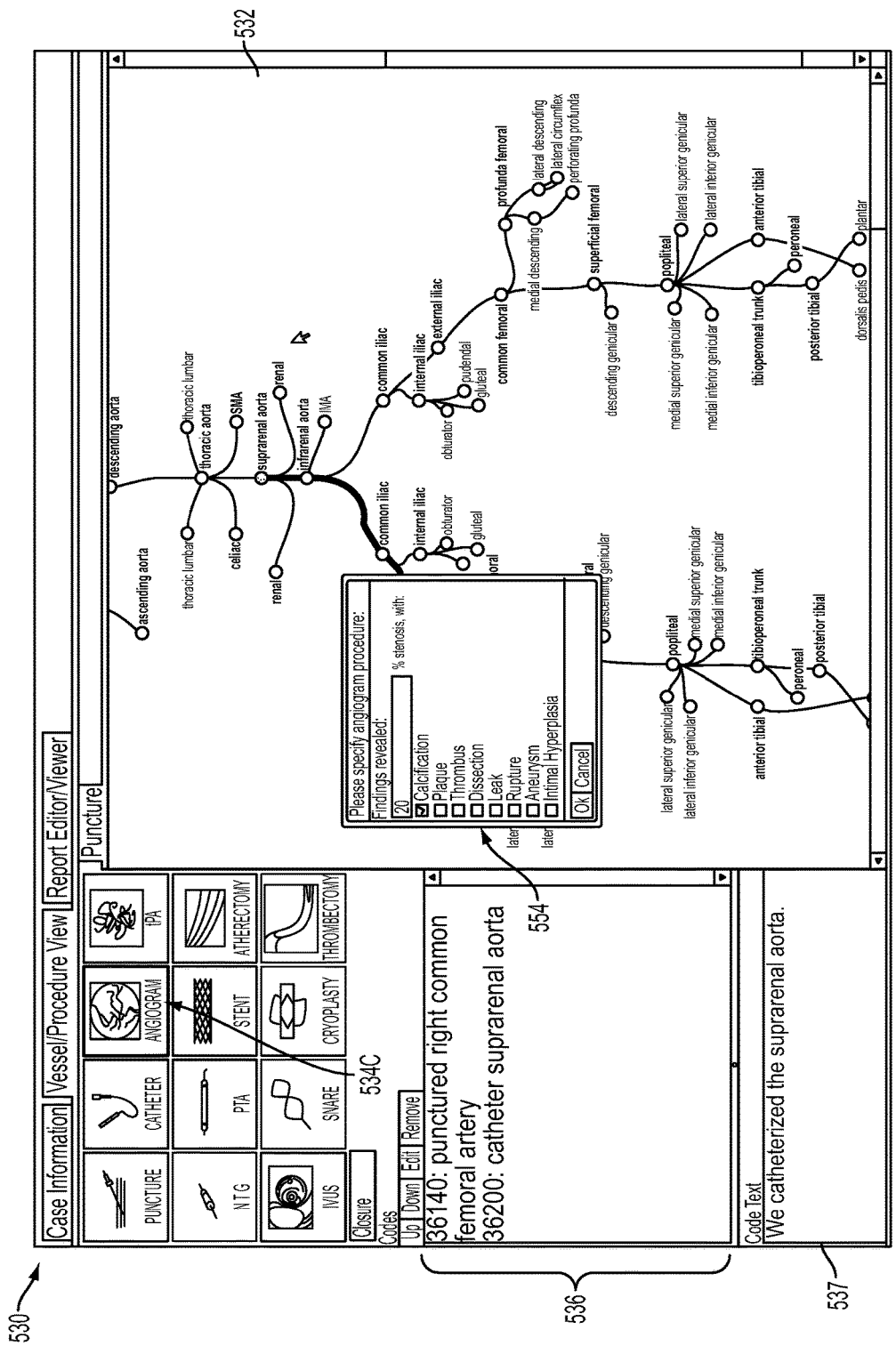

The surgeon may continue to interact with GUI 530 in this manner to document the procedures performed on the patient. For example, further assume that the surgeon selects the angiogram icon, labeled 534C in FIG. 5H, and selects/clicks on the suprarenal aorta. For example, assume that the surgeon performed an angiogram on the suprarenal aorta. In this case, the surgeon may simply move the cursor/mouse to the angiogram icon at area 534C and click or select "enter." Output control logic 320 may also provide a pop-up window 554 prompting the surgeon to specify details of the angiogram procedure. For example, pop-up window 554 may prompt the surgeon to enter findings associated with the angiogram procedure, such as the percentage stenosis, and/or whether calcification, plaque, thrombus, dissection, leak, rupture, aneurysm, intimal hyperplasia, etc., were detected.

Billing code generator logic 330 may also automatically identify codes corresponding to the angiogram procedure in a similar manner as that discussed above with respect to the puncture and catheterization procedures. For example, billing code generator logic 330 may perform a lookup to identify a code corresponding to the angiogram procedure on the suprarenal aorta that was inputted via GUI 530. For example, as described previously, billing code generator logic 330 may include a table of codes that correspond to various procedures. These codes may correspond to HCPCS codes or other codes associated with an insurance provider.

Figure 5I:
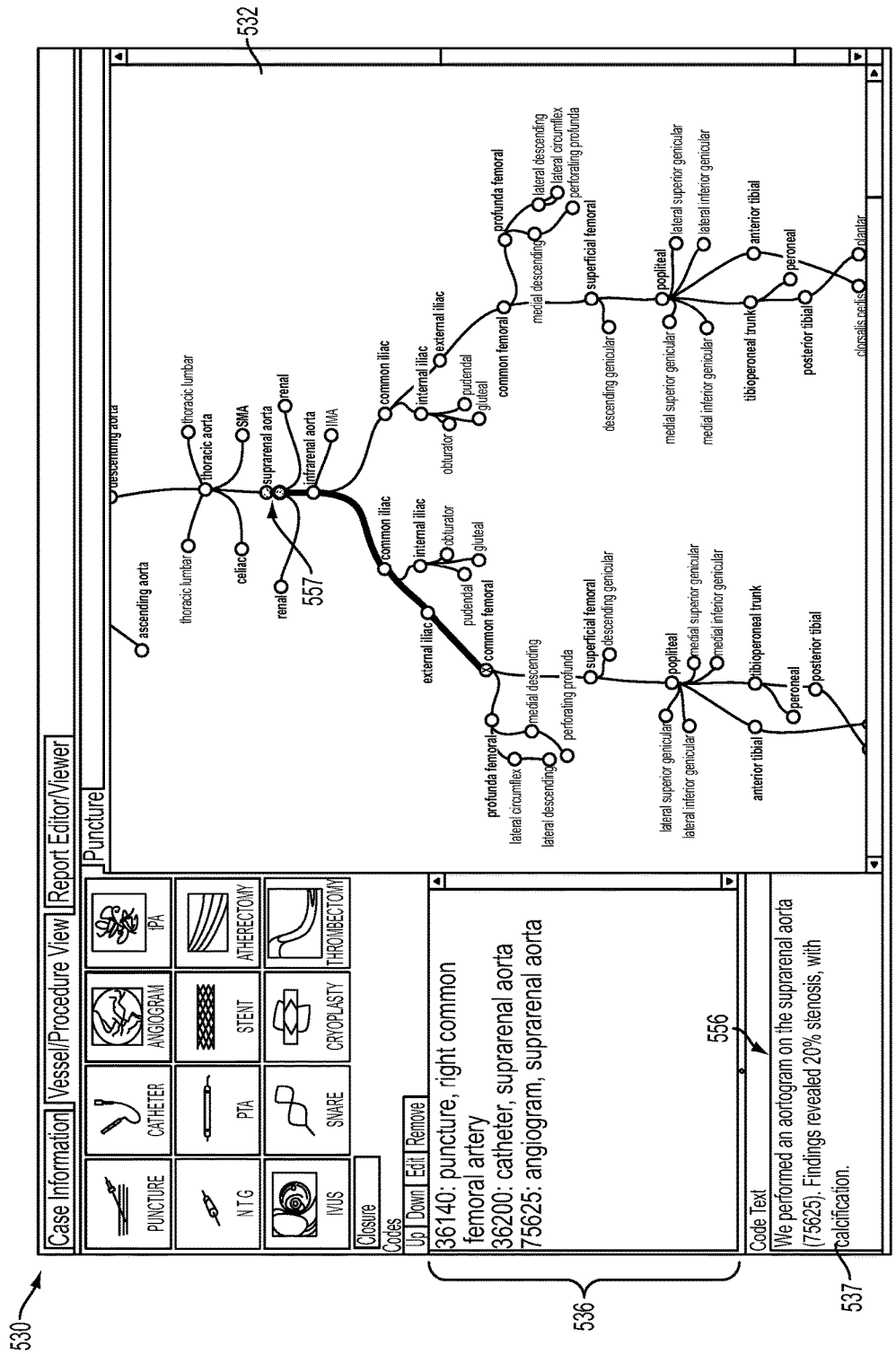

Output control logic 320 may output/display the code identified by billing code generator logic 330 (corresponding to the procedures entered via GUI 530) in codes area 536, as illustrated in FIG. 5I (block 440). For example, output control logic 320 may output "75625: angiogram suprarenal aorta" at area 536. This may indicate to the surgeon that he/she performed an angiogram on the suprarenal aorta and the HCPCS codes for that procedure is 75625. Output control logic 320 may also take the information provided via pop-up window 554 and output all or some of the information provided via pop up window 554 in area 537. For example, text 556 in area 537 may read: "We performed an angiogram on the suprarenal aorta (75625). Findings revealed 20% stenosis, with calcification." This information may correspond to the information provided via pop-up window displayed in FIG. 5H. The surgeon may also augment and/or change the information automatically provided in text area 537.

For example, user interface logic 310 may prompt the surgeon to input text or augment the text provided in area 537 to enhance the information automatically provided in area 537. As an example, the surgeon may add a note regarding other findings associated with the angiogram or percentage stenosis/blockage. As discussed above, report generator 340 may use text displayed in area 537 to generate a narrative that will be included in a report and that will act as a surgeon's operation notes identifying the procedures performed on the patient in chronological order. Such a report may be used by the surgeon at later points in time to review a patient's medical history in a manner consistent with standard clinical requirements. In addition, the report may conform to third party payer requirements and provide needed documentation and/or justification for the procedures that were performed and ultimately billed to the third party (e.g., insurance provider 130).

In some implementations, after the surgeon has selected the angiogram icon 534C and the suprarenal aorta as described above with respect to FIG. 5H, output control logic 320 may provide an icon on the visual representation at area 532 indicating that an angiogram has been performed on the suprarenal aorta. For example, output control logic 320 may provide text/icon "AN" at area 557, as illustrated in FIG. 5I. This provides the surgeon with an easy to understand visual confirmation corresponding to the entered information.

Figure 5J:
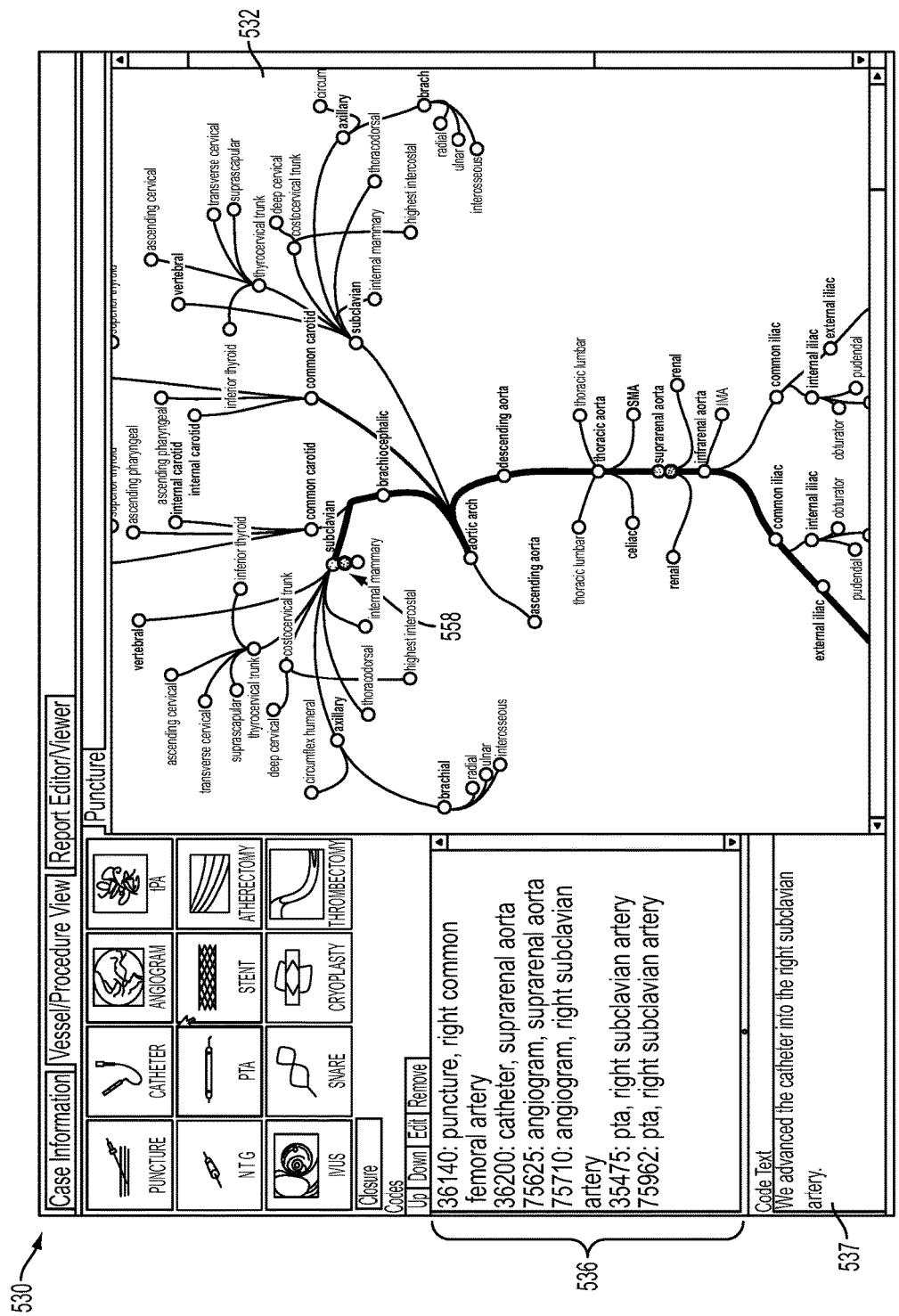

The surgeon may continue to select the appropriate procedures at input area 534, followed by identifying portions of the visual representation of the vascular system (provided in area 532) on which the procedures were performed. Output control logic 320 will highlight the portion of the vascular system and add notations/icons associated with each procedure, as illustrated in FIG. 5J. For example, the surgeon may interact with GUI 530 to input information regarding an angiogram performed on the right subclavian artery, a percutaneous transluminal angioplasty (PTA) procedure performed on the right subclavian artery, etc. The portions of the vascular system which have been selected by the surgeon (and corresponding to portions of the body associated with the surgery), may be highlighted in color, via bolding or via other mechanisms, as illustrated in FIG. 5J. Output control logic 320 may also automatically provide text and/or an icon associated with the procedure on the visual representation. For example, output control logic 320 may provide text/icon "AN" and "P" or "PTA" at area 558, as illustrated in FIG. 5J. Output control logic 320 may also receive from billing code generator logic 330 each code that is associated with the procedures that were performed and input via GUI 530. Output control logic 320 may display the appropriate codes in area 536, as also illustrated in FIG. 5J.

Figure 5K:
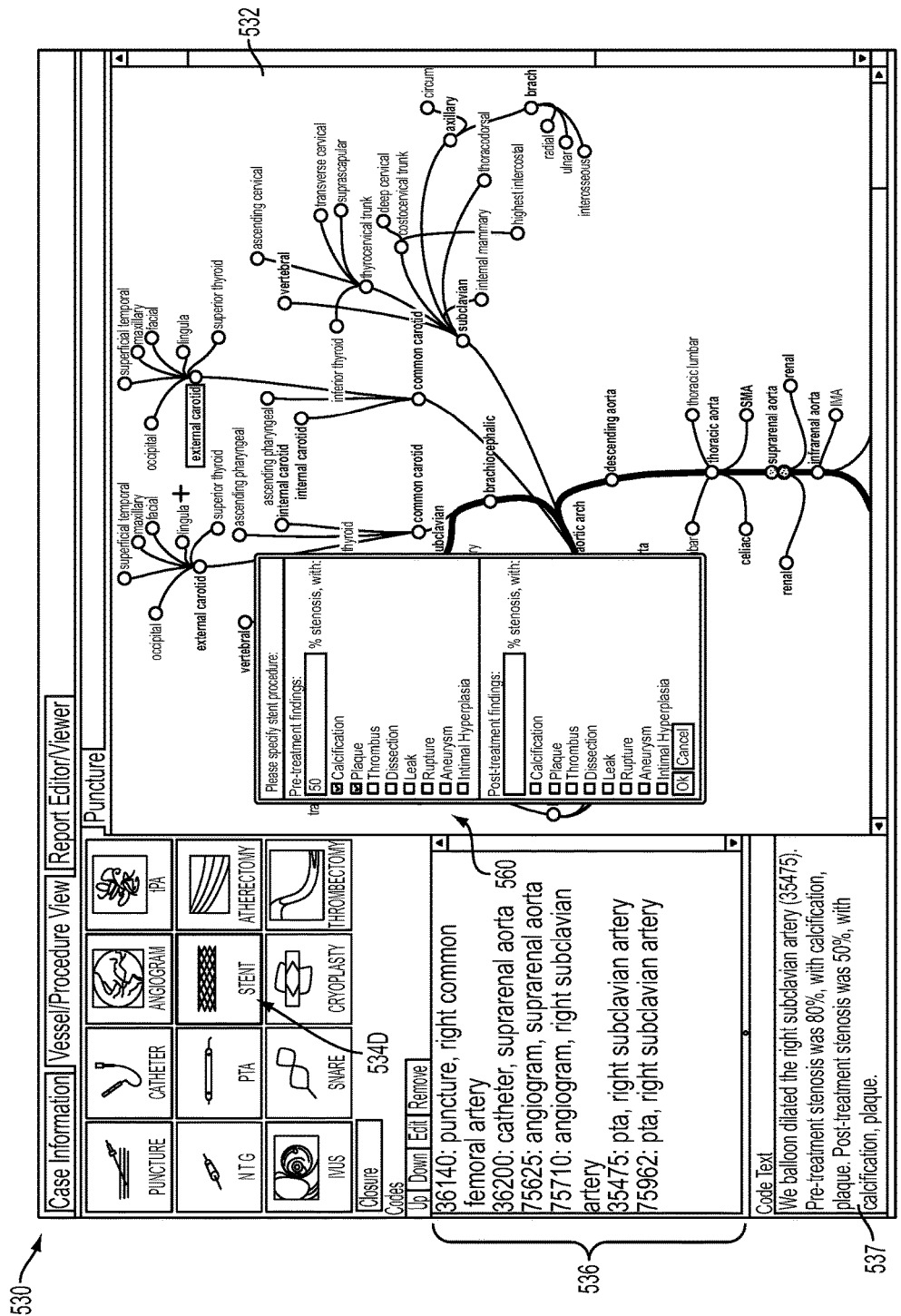

Depending on the particular procedure selected via area 534, output control logic 520 may provide a pop-up or dialog window/box to allow the surgeon to easily provide information regarding the particular procedure. For example, assume that the surgeon selects stent icon, labeled 534D in FIG. 5K. In this case, output control logic 320 may provide pop-up window 560 that allows the surgeon to enter pre-treatment findings, as well as post-treatment findings after the stent procedure was performed. As discussed previously, output control logic 320 may automatically provide some or all of this information in area 537 and/or allow the surgeon to enter information or augment the information provided at area 537 to essentially create a running narrative for the procedure that corresponds to the chronological order of the events performed during the surgery.

As also described above, report generator 340 may automatically use text displayed in area 537 when generating a report that may be submitted to a third party payer. In some instances, the text in area 537 may need to be provided to a third party payer as a way to provide documentation and/or justification for certain procedures performed during the surgery.

Figure 5L:
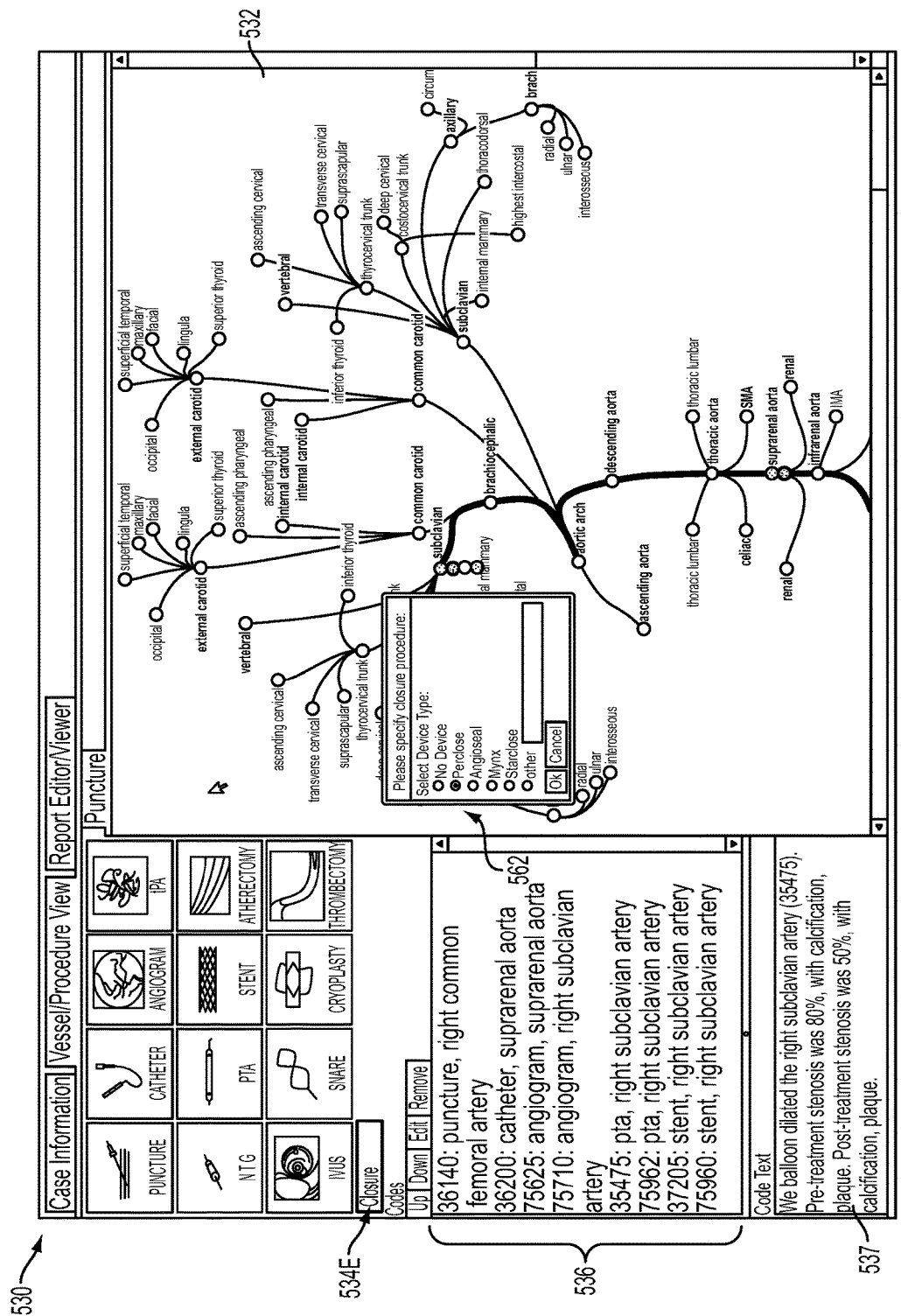

In this example, assume that the surgeon selects the closure box/icon, labeled 534E in FIG. 5L. Output control logic 320 may provide pop-up window 562 prompting the surgeon to enter the type of device used for the closure procedure. This information may then be provided in text area 537. The surgeon may also augment this information as needed.

In each case, GUI 530 allows the surgeon to document the procedures that were performed in a graphical/visual manner and also identify particular codes associated with the procedures that were performed. In this manner, the surgeon may be provided with a clear graphical representation of the surgery, along with text/icons detailing all of the procedures that were performed. In addition, billing code generator logic 330 may identify codes corresponding to each procedure via its stored table of codes (e.g., HCPCS codes) and output control logic 320 may provide the codes in area 536.

In some implementations, output control logic 320 may also highlight codes that correspond to portions of the procedure that may be billed as separate items to a service provider, such as insurance provider 130. For example, in some implementations, codes displayed in area 536 in a heavier font, a bolder font, or in a colored font may correspond to procedures that may be billed. Other ones of the codes shown in area 536 may be lighter in color, which may indicate that these procedures may not be separately billed. This provides the surgeon with a further indication of the billable events associated with the surgery via a graphical mechanism.

After the surgeon has completed providing information documenting the surgical procedure, the surgeon may save the information. For example, GUI 530 may include a control button (not shown) that allows the user to save the information. GUI 310 may also include a control button prompting the user to generate a report for approval by the surgeon. For example, assume that the surgeon elects to save the information entered via GUI 530. In response to the request to save the information, output control logic 320 may display a pop-up window (not shown) in GUI 530 inquiring whether the surgeon would like to generate a report.

Assume that the surgeon elects to generate a report regarding the procedure. Output control logic 320 may then generate a report and save the report to report generator 340. Output control logic 320 may also output the report for display and/or approval by the surgeon (block 450). For example, output control logic 320 may output report 600 illustrated in FIGS. 6A and 6B via output device 270 (e.g., an LCD screen).

Referring to FIGS. 6A and 6B, report 600 may include patient information area 610, pre-operation and post-operation diagnosis area 620, operations titles area 630, surgeon information area 640, description area 650, additional information area 660, signature area 670 and billable codes area 680.

Patient information area 610 may display a patient's name, patient ID, patient's date of birth, date of operation, start time, end time, etc. Pre-operation and post-operation diagnostic codes may display information previously entered by the surgeon. For example, in report 600, pre-operation diagnostic code 440.20 corresponds to the code provided in area 522 in FIG. 5B.

Operations title area 630 may provide descriptive titles associated with the procedures that were performed on the patient. In an exemplary implementation, the titles provided in area 630 may be based on the particular selections made by the user with respect to the procedures, as well as information entered by the surgeon via the pop-up windows.

Surgeon information area 640 may display the name of the surgeon and assistant surgeon, as well as other pertinent information associated with the procedures that were performed (e.g., the type of anesthesia given). Description area 650 may display a running description of all the procedures that were performed. The information in description area may be based on the information displayed to the surgeon in text area 537 for each procedure that was performed. As discussed above, the surgeon may also have augmented or edited the information provided in text area 537 and the added information may also be provided in description area 650 of report 600.

In summary, description area 650 may provide the surgeon with detailed operation notes that describes the events in the order in which they were performed. The information in description area 650 may also provide justification/documentation for performing and billing certain procedures. For example, description area 650 in FIG. 6A indicates that the right subclavian artery was balloon dilated and post-treatment stenosis was 50% with calcification and plaque. This information may correspond to information provided by the surgeon via a pop-up window provided in GUI 530 (e.g., a pop-up window similar to window 560 in FIG. 5K). Description area 650 of report 600 further indicates that the surgeon inserted a stent in the right subclavian artery after the balloon catheterization and that post-treatment findings revealed 0% stenosis. Such information in report 600 may conform to documentation requirements associated with the surgeon being able to bill the third party payer (e.g., insurance provider 130) for both the balloon catheterization and the stent procedure. In other words, the information in description area 650 may be used by the third party payer to determine whether all of the billed procedures were necessary and in accordance with approved medical standards.

Referring to FIG. 6B, additional information area 660 of report 600 may include information provided by the surgeon, such as information inputted at text area 537, such as any complications, blood loss information, etc. Signature area 670 include a signature block for the surgeon to provide his/her signature, such as an electronic signature.

Billable codes area 680 may display a list of all codes associated with billable events. For example, as described above, in some implementations, billing code generator logic 330 may identify procedures that are not separately billable to insurance provider 130. Billing code generator logic 330 may then omit the codes corresponding to these events from billable codes area 680. In each case, the billable codes provided at billable codes area 680 correspond to some or all of the codes displayed at area 536, described above with respect to FIGS. 5D-5L. The billable codes at area 680 may also provide text associated with each of the billable codes. For example, the first billable code 75625 may include the text "angiogram" and "suprarenal aorta" that corresponds to the procedure associated with billable code 75625.

In summary, report 600 provides the surgeon with an easy to understand summary of the surgery and allows the surgeon to quickly determine if he/she has provided all the input associated with the surgery. If the surgeon wishes to change or augment information provided in report 600, the surgeon may manually enter the information.

Report 600 may also provide a template that is formatted with content designed to satisfy third party payer (e.g., insurance provider 130) requirements regarding appropriate documentation for various medical procedures. As described previously with respect, output control logic 320 may automatically determine which ones of the procedures performed by the surgeon are billable. For example, some insurance providers require that only certain procedures performed by a surgeon may be itemized as a separately billable item. Output control logic 320 may store these payer rules regarding medical procedures and codes associated with the medical procedures to ensure that information corresponding to separately billable events are ultimately billed to any number of potential third party payers. As also discussed, in some implementations, these billable events may be shown in a bolder font or different color font in codes area 536 of GUI 530, as compared to non-billable events/codes. In some implementations, the description in description area 650 may also provide documentation needed by the third party payer to approve the surgeon's bill.

The surgeon may review the report, add/change information in report 600 and forward report 600, including the list of billable codes and the description of the procedures performed to the insurance provider (block 450). For example, in one implementation, the surgeon may provide his/her electronic signature at area 670 and forward the report 600 to insurance provider 130 via network 140.

In this manner, a surgeon may be above to easily enter information regarding a surgery via a GUI and billing program 300 may automatically generate the required billing information. In addition, by automatically generating the operative notes regarding the procedures performed with sufficient detailed description to satisfy third party payers' requirements regarding appropriate documentation, denial of payment for reasons including lack of adequate documentation may be eliminated. Report generator 340 may also be used to create a database for storing statistics and other information regarding medical procedures. For example, a surgeon may access report generator 340 to compile statistics regarding procedures performed over a period of time for research and/or other purposes.

CONCLUSION

Implementations described herein provide a billing program that allows users to generate billing information associated with medical procedures, as well as provide corresponding operation/procedure notes consistent with the medical procedures that were preformed. Advantageously, by providing a visual/graphical interface, the doctor and/or other medical professional are much less likely to forget to include acts performed during the surgery. In addition, by automatically generating billing codes, the time spent manually attempting to identify the appropriate billing codes is basically eliminated. In addition, by automatically generating the notes associated with the procedures that were performed (e.g., operation or surgery related procedures), the need for the doctor to dictate or write out the procedure notes, as well as the need for other staff members to transcribe the dictation or modify the procedure notes may be eliminated. Further, by having the billing program generate both the billing information and the operation nodes, implementations consistent with the invention ensure that all billable procedures are consistently and appropriately documented, thereby reducing the likelihood of denial of payments by payers based on inadequate documentation.

The foregoing description of exemplary implementations provides illustration and description, but is not intended to be exhaustive or to limit the invention to the precise form disclosed. Modifications and variations are possible in light of the above teachings or may be acquired from practice of the invention.

For example, various features have been described above with respect to a surgeon interacting with billing program 300 after a surgery. In other implementations, other medical personnel (e.g., a nurse, staff person, etc.) may interact with billing program 300 to input the desired information. In still other implementations, a staff person or the doctor may input information to billing program 300 during the medical procedure (e.g., during the surgery). In some instances, billing program 300 may include voice recognition software that facilitates entry of information via one or more of the GUIs described above.

In addition, features have been described above with respect to a particular GUI provided to a surgeon, such as a vascular surgeon. In other implementations, other visual GUIs may be provided based on the particular type of doctor and/or medical procedure being performed. For example, a cardiac surgeon may be provided with a different GUI than GUI 530 illustrated in FIGS. 5D-5L, and an orthopedic surgeon may be provided with still a different GUI. Still further, a general family physician may be provided with a different GUI than a specialist. In addition, a dentist may use billing program 300 and be provided with a GUI based on different types of dental procedures that may be performed. In each case, billing program 300 may provide a GUI based on the type of doctor and types of procedures typically performed by that type of doctor.

In addition, although not described in detail above, billing program 300 may be used with a number of different languages. For example, the user may select a language preference (e.g., English, Spanish, French, etc.) via an initial GUI and billing program 300 may provide additional GUIs and reports in the desired language.

In addition, the functions described above as being performed by a particular device or logic component may be performed by another device/logic component in other implementations. In addition, functions described as being performed by a single device may be performed by multiple devices, or vice versa.

Further, while series of acts have been described with respect to FIG. 4, the order of the acts may be varied in other implementations. Moreover, non-dependent acts may be implemented in parallel.

It will be apparent to one of ordinary skill in the art that various features described above may be implemented in many different forms of software, firmware, and hardware in the implementations illustrated in the figures. The actual software code or specialized control hardware used to implement the various features is not limiting of the invention. Thus, the operation and behavior of the features of the invention were described without reference to the specific software code—it being understood that one of ordinary skill in the art would be able to design software and control hardware to implement the various features based on the description herein.

Further, certain portions of the invention may be implemented as "logic" that performs one or more functions. This logic may include hardware, such as a processor, a microprocessor, an application specific integrated circuit, or a field programmable gate array, software, or a combination of hardware and software.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A non-transitory computer-readable medium having stored thereon sequences of instructions which, when executed by at least one processor, cause the at least one processor to:
   output a graphical user interface (GUI), the GUI including a visual representation of at least a portion of a human body and a text input area;
   receive input from a user via the GUI, the input selecting portions of the visual representation and identifying a sequence of medical procedures that were performed on a patient with respect to the selected portions;
   highlight the selected portions on the visual representation, the highlighted portions providing a graphical representation of the sequence of medical procedures that were performed on the patient;
   automatically generate billing codes corresponding to the medical procedures that were performed based on the input received via the GUI;
   automatically generate text, based on input received via the GUI, identifying at least some of the medical procedures that were performed;
   display the billing codes and the generated text on the GUI;
   provide, via the GUI, a pop-up or dialog window in response to input corresponding to at least some of the medical procedures that were performed;
   receive, from the user, information via the pop-up or dialog window;
   display at least some of the information provided via the pop-up or dialog window in the text input area of the GUI;
   wherein the sequence of medical procedures corresponds to surgery performed on the patient and the visual representation displays a portion of a vascular system of the human body, and
   wherein when highlighting the selected portions, the instructions cause the at least one processor to highlight a path in the displayed portion of the vascular system corresponding to portions of the vascular system in which the surgery was performed;
   determine which of the medical procedures that were performed on the patient are billable; and
   generate a report including particular ones of the billing codes corresponding to medical procedures determined to be billable.

2. The non-transitory computer-readable medium of claim 1, wherein when generating the report, the instructions cause the at least one processor to:
   include text other than the billing codes in the report regarding the medical procedures that were performed, based on a third party's payer requirements associated with paying for medical procedures.

3. The non-transitory computer-readable medium of claim 1, wherein the instructions further cause the at least one processor to:
   access a database to identify particular ones of the billing codes that correspond to medical procedures that were performed on the patient that are not separately billable; and wherein when generating the report, the instructions cause the at least one processor to:
   omit, from the report, billing codes that correspond to the medical procedures that were performed and are not separately billable.

4. The non-transitory computer-readable medium of claim 1, wherein the instructions further cause the at least one processor to:
   prompt the user to provide information based on each of the medical procedures that were performed; and
   generate the report, in response to a request from the user, the report including information provided by the user in response to the prompt.

5. The non-transitory computer-readable medium of claim 1, wherein the text input area is configured to receive, from the user, input information associated with the medical procedures that were performed.

6. The non-transitory computer-readable medium of claim 1, wherein the instructions cause the at least one processor to:
annotate the visual representation to display text or icons based on the medical procedures that were performed.

7. The non-transitory computer-readable medium of claim 1, wherein the billing codes comprise Healthcare Common Procedure Coding System (HCPCS) codes or codes associated with other systems.

8. A method, comprising:
outputting, by a computer device, a graphical user interface (GUI), the GUI including a visual representation of at least a portion of a human body;
receiving, by the computer device, input from a user via the GUI, the input selecting portions of the visual representation and identifying a sequence of medical procedures that were performed on a patient with respect to the selected portions;
highlighting, simultaneously, by the computer device, the selected portions of the visual representation, the highlighted portions providing a graphical representation of the sequence of medical procedures that were performed on the patient, wherein highlighting the selected portions comprises highlighting a path in a portion of a vascular system in which a surgery was performed;
providing, by the computer device and via the GUI, at least one of icons or text corresponding to the medical procedures that were performed;
automatically generating, by the computer device, billing codes corresponding to the medical procedures that were performed;
automatically generating text, by the computer device and based on input received via the GUI, identifying the medical procedures that were performed;
displaying, by the computer device, the billing codes and the generated text on the GUI;
providing, via the GUI, a pop-up or dialog window in response to input corresponding to a selection of a particular one of the medical procedures that was performed;
receiving, from the user, information via the pop-up or dialog window;
displaying at least some of the information provided via the pop-up or dialog window on the GUI;
determining which of the medical procedures that were performed on the patient are billable; and
generating a report including particular ones of the billing codes corresponding to medical procedures determined to be billable.

9. The method of claim 8, wherein the generating a report comprises:
identifying a third party's payer requirements associated with the medical procedures that were performed; and
including text in the report based on the identified third party's payer requirements.

10. The method of claim 8, further comprising:
identifying, based on the determining, billing codes that correspond to particular ones of the medical procedures that are not separately billable; and
omitting, from the report, the billing codes that correspond to medical procedures that are not separately billable.

11. The method of claim 8, further comprising:
prompting the user to provide information based on the particular medical procedures that were performed; and
generating the report, in response to a request from the user, the report including information provided by the user in response to the prompting.

12. The method of claim 8, wherein the GUI includes a text input area configured to receive, from the user, input information regarding each of the medical procedures that were performed.

13. The method of claim 12, wherein the pop-up or dialog window requests particular information from the user based on the particular medical procedure, the method further comprising:
displaying the at least some of the information provided via the pop-up or dialog window in the text input area of the GUI.

14. The method of claim 8, wherein the billing codes comprise Healthcare Common Procedure Coding System (HCPCS) codes or codes associated with other systems.

15. A system, comprising:
a non-transitory computer-readable memory configured to store instructions;
a display; and
a processor configured to execute the instructions to:
output a graphical user interface (GUI) via the display, the GUI including a visual representation of at least a portion of the human body;
receive input from a user via the GUI, the input selecting portions of the visual representation and identifying a sequence of medical procedures performed on a patient with respect to the selected portions;
highlight, simultaneously, the selected portions on the visual representation, the highlighted portions providing a graphical representation of the sequence of medical procedures that were performed on the patient, wherein when highlighting the selected portions, the instructions cause the processor to highlight a path in a portion of a vascular system in which a surgery was performed;
automatically generate billing codes corresponding to the medical procedures that were performed;
automatically generate text, based on input received via the GUI, identifying at least some of the medical procedures that were performed;
display the billing codes and the generated text on the GUI;
provide, via the GUI, a pop-up or dialog window in response to input corresponding to at least some of the medical procedures that were performed;
receive, from the user, information via the pop-up or dialog window;
display at least some of the information provided via the pop-up or dialog window on the GUI;
determine which of the medical procedures that were performed on the patient are billable; and
generate a report including particular ones of the billing codes corresponding to medical procedures determined to be billable.

16. The system of claim 15, wherein the processor is further configured to:
include text in the report that conforms with a third party's payer requirements.

17. The non-transitory computer-readable medium of claim 1, wherein the generated text provides a narrative for the sequence of medical procedures.

18. The system of claim 15, wherein the sequence of medical procedures corresponds to the surgery performed on the patient and the visual representation displays the portion of the vascular system of the human body.

* * * * *